(12) United States Patent
Kunitani et al.

(10) Patent No.: US 7,084,262 B2
(45) Date of Patent: *Aug. 1, 2006

(54) ANALYSIS AND SEPARATION OF PLATELET-DERIVED GROWTH FACTOR PROTEINS

(75) Inventors: Michael Kunitani, Corte Madera, CA (US); An D. Tran, Moraga, CA (US); Hugh Parker, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 699 days.

This patent is subject to a terminal disclaimer.

(21) Appl. No.: 10/205,693

(22) Filed: Jul. 26, 2002

(65) Prior Publication Data

US 2003/0036511 A1    Feb. 20, 2003

Related U.S. Application Data

(60) Continuation of application No. 09/549,290, filed on Apr. 14, 2000, now Pat. No. 6,448,382, which is a division of application No. 08/989,250, filed on Dec. 12, 1997, now Pat. No. 6,083,910.

(60) Provisional application No. 60/032,720, filed on Dec. 13, 1996.

(51) Int. Cl.
*C07K 14/49* (2006.01)
*A61K 38/18* (2006.01)

(52) U.S. Cl. .................. 530/412; 530/416; 530/399; 435/69.1; 435/254.21

(58) Field of Classification Search ............... None
See application file for complete search history.

(56) References Cited

U.S. PATENT DOCUMENTS 5,094,941 A * 3/1992 Hart ..................... 435/7.9

FOREIGN PATENT DOCUMENTS

| EP | 0 259 632 A1 | 3/1988 |
|---|---|---|
| EP | 0 547 064 B1 | 6/1994 |
| WO | WO 90/08163 | 7/1990 |
| WO | WO 92/01716 | 7/1991 |

OTHER PUBLICATIONS

Watson and Kenney (1992) J. Chromatography 606:165-170.*
Soma et al., FASEB Journal: official publication of the Federation of American Societies for Experimental Biology, (Aug. 1992) 6(11) 2996-3001.*
Cook, A.L., et al., Purification and Analysis of Proteinase-Resistant Mutants of Recombinant Platelet-Derived Growth Factor-BB Exhibiting Improved Biological Activity, *Biochemical Journal*, 1992, pp. 56-65, vol. 281(1).
Oefner, C., et al., "Crystal Structure of Human Platelet-Derived Growth Factor BB," *EMBO Journal*, 1992, pp. 3921-3926, vol. 11.

* cited by examiner

*Primary Examiner*—Eileen B. O'Hara
(74) *Attorney, Agent, or Firm*—Leslie T. Henry; Lisa E. Alexander; Alisa A. Harbin

(57) ABSTRACT

Methods for improving purification and quantification of platelet derived growth factor (PDGF) proteins having structural heterogeneity are provided. Preparation of substantially pure isoforms of these proteins is achieved using TSK sulfopropyl cation exchange chromatography and reverse phase high performance liquid chromatography. A reverse charged capillary zone electrophoresis method enables quantification of substantially pure isoforms of these proteins resulting from endoproteolytic post-translational modifications. Compositions of the invention are substantially purified isoforms of secreted PDGF proteins having structural heterogeneity, more particularly purified intact, single-clipped, and double-clipped isoforms of recombinant PDGF-BB. Pharmaceutical compositions comprising at least one of these substantially purified recombinant PDGF isoforms and methods for their use in promoting wound healing are also provided.

6 Claims, 6 Drawing Sheets

Schematic representation of isoforms of intact rhPDGF-BB resulting from truncation of Thr-109

A

• Thr-109 truncation

Schematic representation of isoforms of single clipped rhPDGF-BB resulting from truncation of Arg-32 and Thr-109

■ Arg-32 truncation

● Thr-109 truncation

Isoforms of double clipped rhPDGF-BB resulting from truncation of Arg-32 and Thr-109

■ Arg-32 truncation
● Thr-109 truncation

High Temperature RP-HPLC of rhPDGF-BB (Reference Standard Lot MPAPK005) using a Linear Gradient Elution A  DC and truncated DC isoforms of rhPDGF-BB
B  SC and truncated SC isoforms of rhPDGF-BB
C  IN and truncated IN isoforms of rhPDGF-BB High Temperature RP-HPLC of rhPDGF-BB (Reference Standard Lot MPAPK005) using a Step Gradient Elution A   DC and truncated DC isoforms of rhPDGF-BB
B   SC and truncated SC isoforms of rhPDGF-BB
C   IN and truncated IN isoforms of rhPDGF-BB
D   rhPDGF-BB dimer/dimer

ANALYSIS AND SEPARATION OF PLATELET-DERIVED GROWTH FACTOR PROTEINS

CROSS-REFERENCE TO RELATED APPLICATIONS

The present application is a continuation of U.S. application Ser. No. 09/549,290, filed Apr. 14, 2000, now U.S. Pat. No. 6,448,382, which is a divisional of U.S. application Ser. No. 08/989,250, filed Dec. 12, 1997, now U.S. Pat. No. 6,083,910, which claims the benefit of U.S. application Ser. No. 60/032,720, filed Dec. 13, 1996, the contents of which are herein incorporated by reference in their entirety.

FIELD OF THE INVENTION

The present invention relates to the field of protein analysis and separation, particularly to preparations of purified isoforms of heterologous proteins having structural heterogeneity.

BACKGROUND

Platelet-derived growth factor (PDGF), the primary mitogen in serum for mesenchymal-derived cells, is stored in platelet alpha-granules. Injury to blood vessels activates the release of PDGF from these granules in the vicinity of the injured vessels. This mitogen acts as a potent chemoattractant for fibroblasts and smooth muscle cells, as well as monocytes and neutrophils. The mitogenic activity of the localized PDGF results in proliferation of these cells at the site of injury, contributing to the process of wound repair.

Purified native platelet-derived growth factor (PDGF), a glycoprotein of about 30,000 daltons, is composed of two disulfide-linked polypeptide chains. Two forms of these chains, designated A and B, have been identified. The native protein occurs as the homodimer AA or BB or the heterodimer AB, or a mixture thereof. A partial amino acid sequence for the PDGF-A chain has been identified (Johnsson et al. (1984) *EMBO J.* 3:921–928) and cDNAs encoding two forms of PDGF A-chain precursors have been described (U.S. Pat. No. 5,219,759). The mature A-chain consists of a 104 amino acid polypeptide that is derived by proteolytic processing of a 211 amino acid precursor polypeptide. The cDNA encoding the PDGF-B chain has also been described (*Nature* (1985) 316:748–750). The mature B-chain consists of a 109 amino acid polypeptide that is derived by proteolytic processing of a 241 amino acid precursor polypeptide. The mature A and B chains of PDGF show sequence identity of 51%, with the eight cysteine residues being conserved in each of the chains (Johnsson et al. (1984) *EMBO J.* 3:921–928).

In addition to proteolytic processing of the precursor polypeptides into mature PDGF-A and PDGF-B chains, recombinant PDGF (rPDGF) produced in a yeast host undergoes further post-translational processing that results in a secreted mature protein having considerable structural heterogeneity. This is true for the heterodimer rPDGF-AB, and more particularly for the homodimer rPDGF-BB.

When expressed in a yeast host for production of a bulk drug substance, PDGF undergoes endoproteolytic cleavage, or so-called clipping, of the B-chain between the Arg-32 and Thr-33 residues, resulting in a bulk drug substance having a mixture of unclipped or so-called intact rPDGF and clipped rPDGF that has been cleaved in the B-chain between the Arg-32 and Thr-33 residues. In the case of rPDGF-BB, one or both of the B-chains may be clipped, resulting in single-clipped or double-clipped rPDGF-BB, respectively. Other post-translational modifications of interest to the present invention include exoproteolytic removal of C-terminal amino acids, or so-called truncation, which may remove Arg-32 from clipped B-chains and/or Thr-109 from intact and clipped B-chains. These post-translational modifications lead to a number of structural forms, or so-called isoforms, of rPDGF-BB present in the secreted product. Methods of the present invention are directed to separation and purification of the intact, single-clipped, and double-clipped isoforms of rPDGF, more particularly rPDGF-BB.

The three dimeric forms of PDGF exhibit different binding affinities for the two known PDGF receptor gene products, $\alpha$ and $\beta$. The beta receptor recognizes PDGF B chain and is dimerized in the presence of PDGF-BB. The alpha receptor recognizes PDGF B and A chains and can be dimerized by PDGF-BB, PDGF-AA, and PDGF-AB (see, for example, Abboud et al (1994) *J. Cell. Phys.* 158:140–150). The amino acid residue region of PDGF-BB involved in binding or activation of the receptor has been narrowed down to residues Ile25-Phe37 (Giese et al. (1990) *Mol. Cell. Biol.* 10:5496–5501). These residues include the Arg-32/Thr-33 site cleaved by endoproteolytic processing during production of PDGF-BB by a yeast host.

Proteinase-resistant mutants of recombinant PDGF-BB exhibiting improved biological activity have been identified (Cook et al. (1992) *Biochem. J.* 281:57–65; see also European Patent Application No. 0 547 064 B1). These mutants prevent endoproteolytic cleavage of the B-chains at Arg-32. Thus elimination of endoproteolytic cleavage in this region apparently leads to increased biological activity of the PDGF-BB produced in a yeast host during the fermentation process. This increase in biological activity is presumably associated with an increase in the relative amount of unclipped, or so-called intact, PDGF-BB and a decrease in the relative amount of clipped PDGF-BB in the recombinant PDGF-BB product. Similarly, endoproteolytic cleavage in this region of either or both of the B-chains within a rPDGF-BB protein would be expected to yield a bulk drug substance having different biological activity than found for a bulk drug substance consisting solely of the intact rPDGF-BB.

Prior to the present invention, methods commonly used in the art to purify recombinantly produced PDGF have not distinguished between the various isoforms of PDGF resulting from post-translational processing, including endoproteolytic cleavage of the PDGF-B chain between Arg-32 and Thr-33. Prior art teaches that structural isoforms resulting from post-translational endoproteolytic cleavage could have varying degrees of biological activity, and hence can effect the overall biological activity of bulk drug substance produced by fermentation.

Methods are needed to separate and quantify the structural isoforms of recombinantly produced PDGF such that their biological activities can be compared. These methods would be useful in preparing bulk drug substances consisting of pure isoforms.

SUMMARY OF THE INVENTION

Methods for improving purification and quantification of platelet derived growth factor (PDGF) proteins having structural heterogeneity are provided. Preparation of substantially pure isoforms of these proteins is achieved using TSK sulfopropyl cation exchange chromatography and reverse phase high performance liquid chromatography. These methods are particularly useful for separating isoforms that result from post-translational endoproteolytic processing of secreted recombinant PDGF (rPDGF), more particularly rPDGF-BB. A reverse charge capillary zone electrophoresis method of the invention is useful for quantifying endoproteolytic post-translational modifications.

Compositions of the invention are substantially purified isoforms of secreted PDGF proteins having structural heterogeneity, more particularly purified intact, single-clipped, and double-clipped isoforms of PDGF-BB. Pharmaceutical compositions comprising at least one of these substantially purified PDGF isoforms and methods for their use in promoting wound healing are also provided.

DETAILED DESCRIPTION OF THE INVENTION

Figure 1:
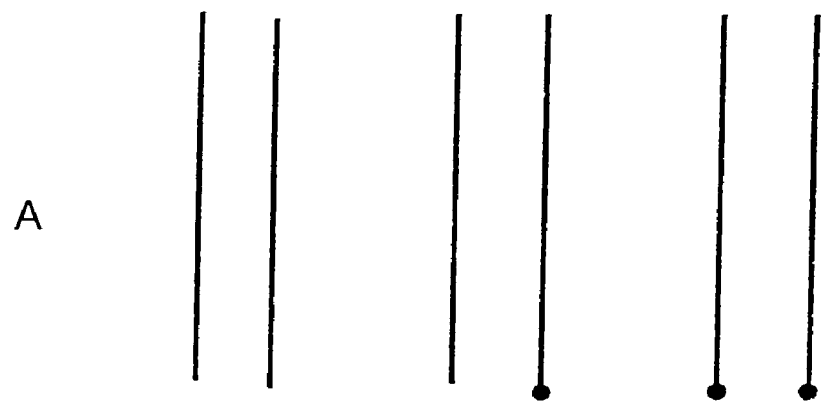
FIG. 1 is a schematic representation of intact isoforms of rhPDGF-BB (group A) with or without truncation of Thr-109. Single lines represent B chains; paired lines represent rhPDGF-BB.

The present invention is directed to compositions having PDGF activity that are useful as therapeutic agents in the treatment of wounds. More specifically, these compositions comprise at least one biologically active, substantially purified isoform of a recombinant PDGF (rPDGF) protein. By "recombinant" is intended the protein is produced as a heterologous or foreign protein in the cells of a host organism stably transformed with a nucleotide sequence encoding the foreign PDGF protein of interest.

Methods of the invention provide for the separation of biologically active isoforms of rPDGF from a bulk drug substance comprising a mixture of these isoforms. The methods are particularly useful for separating isoforms that result from post-translational endoproteolytic processing of secreted rPDGF, more particularly rPDGF-BB. Once separated, isoforms can be substantially purified and incorporated into a pharmaceutical composition for use in treatment of wounds.

An isoform of a rPDGF protein is "biologically active" when it has the capability of performing one or more biological functions or a set of activities normally attributed to PDGF in a biological context. These biological activities include inducing chemotaxis and/or mitogenesis of responsive cell types following the binding of PDGF to a specific cell surface receptor. Other biological activities of PDGF may include, but are not limited to phospholipase activation, increased phosphotidylinositol turnover and prostaglandin metabolism, stimulation of both collagen and collagenase synthesis by responsive cells, indirect proliferative response of cells lacking PDGF receptors, and potent vasoconstrictor activity. Biological activity can be determined using any number of assays available in the art for PDGF, including but not limited to the mitogenic assay described herein.

By "substantially purified isoform" is intended at least about 80%, preferably at least about 90%, more preferably at least about 95% of the composition comprising rPDGF is the isoform of interest. Substantially purified isoforms of a protein are obtained using methods of the present invention that provide for separation of the isoform of interest from a cell culture comprising a mixture of rPDGF isoforms. By "separation of the isoform of interest" is intended removal of any undesirable isoforms or other components in the cell culture such that the remaining isoform is substantially purified.

The rPDGF protein whose isoforms are separated using methods of the present invention will be a biologically active dimeric form, more particularly the homodimer rPDGF-AA and PDGF-BB or the heterodimer rPDGF-AB, as well as any substantially homologous and functionally equivalent variants thereof. By "variant" is intended a protein derived from the native protein by deletion or addition of one or more amino acids to the N-terminal or C-terminal end of the native protein; deletion or addition of one or more amino acids at one or more sites in the native protein; or substitution of one or more amino acids at one or more sites in the native protein. Conservative substitutions that preserve the general charge, hydrophobicity/hydrophilicity, and/or steric bulk of the amino acid substituted may be preferred. Such substitutions may be made, for example, between the members of the following groups: Gly⇔Ala, Val⇔Ile⇔Leu, Asp⇔Glu, Lys⇔Arg, Asn⇔Gln, and Phe⇔Trp⇔Tyr. Other substitutions may be made to eliminate nonessential amino acid residues, such as to alter a glycosylation site, a phosphorylation site, an acetylation site, or to alter the folding pattern by altering the position of a cysteine residue that is not necessary for function. Methods for such manipulations are generally known in the art.

For example, amino acid sequence variants of the PDGF protein of interest can be prepared by mutations in the DNA sequence encoding the native PDGF protein. Methods for mutagenesis and nucleotide sequence alterations are well known in the art. See, for example, Kunkel (1985) *Proc. Natl. Acad. Sci. USA* 82:488–492; Kunkel et al. (1987) *Methods Enzymol.* 154:367–382; U.S. Pat. No. 4,873,192; Walker and Gaastra, eds. (1983) *Techniques in Molecular Biology* (MacMillan Publishing Company, New York) and the references cited therein; herein incorporated by reference. Such variants will continue to possess the desired biological activity. Obviously, the mutations that will be made in the DNA encoding the variant PDGF protein must not place the sequence out of reading frame and preferably will not create complementary regions that could produce secondary mRNA structure. See EP Patent Application Publication No. 75,444.

Thus rPDGF proteins whose isoforms are separated using methods of the present invention include the naturally occurring PDGF proteins as well as variants thereof. These variants will be substantially homologous and functionally equivalent to their native PDGF protein. A variant of a native PDGF protein is "substantially homologous" to the native protein when at least about 80%, more preferably at least about 90%, and most preferably at least about 95% of its amino acid sequence is identical to the amino acid sequence of the native PDGF protein. Variants may differ by about 1, 2, 3, or 4 amino acids. By "functionally equivalent" is intended that the sequence of the variant defines a chain that produces a protein having substantially the same biological activity as the native protein of interest. Such functionally equivalent variants that comprise substantial sequence variations are also encompassed by the invention. Thus a functionally equivalent variant of the native protein will have a sufficient biological activity to be therapeutically useful. by "therapeutically useful" is intended effective in achieving a therapeutic goal, as, for example, healing a wound.

Methods are available in the art for determining functional equivalence. Biological activity can be measured using assays specifically designed for measuring activity of the native protein. Additionally, antibodies raised against the biologically active native protein can be tested for their ability to bind to the functionally equivalent analog, where effective binding is indicative of a protein having a conformation similar to that of the native protein.

Methods of the present invention provide for improved separation and purification of isoforms of rPDGF proteins, more particularly those isoforms resulting from post-translational endoproteolytic processing of rPDGF. The rPDGF whose isoforms are separated may be the homodimer PDGF-BB or the heterodimer PDGF-AB. In one preferred embodiment, the isoforms of recombinant human PDGF (rhPDGF) protein are separated and purified using methods of the invention.

The nucleotide sequence encoding the rPDGF protein whose isoforms are separated using methods of the present invention may be a genomic, cDNA, or synthetic DNA sequence. The genes encoding the native forms of PDGF have been sequenced, and various analogs are well known in the art. Expression of PDGF homodimers and heterodimers is described in, for example, U.S. Pat. Nos. 4,766,073; 4,769,328; 4,801,542; 4,845,075; 4,849,407; 5,045,633; 5,128,321; and 5,187,263; herein incorporated by reference. Based on the known amino acid sequences for the A- and B-chain polypeptides, synthetic nucleotide sequences encoding PDGF A-chain and B-chain polypeptides may be made in vitro using methods available in the art. See particularly Sambrook et al. (1989) *Molecular Cloning: A Laboratory Manual* (Cold Spring Harbor, N.Y.). Where the recombinant PDGF protein of interest is the heterodimer rhPDGF-AB, the nucleotide sequences encoding the hybrid precursor polypeptides comprising the A- and B-chain polypeptides may be assembled as part of one expression cassette or assembled into separate expression cassettes for cotransformation of a host cell.

The nucleotide sequence encoding a recombinant PDGF protein of interest can be expressed in a suitable expression system for subsequent separation and purification of isoforms of interest according to methods of the present invention. Methods are available in the art for expressing heterologous proteins, more particularly for expressing recombinant PDGF homodimers and heterodimers in bacteria (see, for example, Hoppe et al. (1990) *Eur. J. Biochem* 187:207–214; Fretto et al. (1993) *J. Biol. Chem.* 268: 3625–3631), yeast (Kelly et al. (1984) *EMBO J.* 4:3399–3405; Ostman et al. (1989) *Growth Factors* 1:271–281), and mammalian cells (see, for example, Ostman et al. (1988) *J. Biol. Chem.* 263:16202–16208). See also EP 177,957; U.S. Pat. Nos. 5,219,759 and 6,017,731; and the copending patent application entitled "Method for Expression of Heterologous Proteins in Yeast," Ser. No. 09/340,250; herein incorporated by reference. Methods of the present invention may be practiced with rPDGF produced in any host system where post-translational endoproteolytic processing leads to a secreted rPDGF product comprising a mixture of isoforms.

Problems with post-translational proteolytic processing and generation of isoforms are frequently encountered in rPDGF produced in a yeast host. By "yeast" is intended ascosporogenous yeasts (Endomycetales), basidiosporogenous yeasts, and yeast belonging to the Fungi Imperfecti (Blastomycetes). The ascosporogenous yeasts are divided into two families, Spermophthoraceae and Saccharomycetaceae. The later is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces,* and *Saccharomyces*). The basidiosporogenous yeasts include the genera *Leucosporidium, Rhodosporidium, Sporidiobolus, Filobasidium,* and *Filobasidiella*. Yeast belonging to the Fungi Imperfecti are divided into two families, Sporobolomycetaceae (e.g., genera *Sporobolomyces, Bullera*) and Cryptococcaceae (e.g., genus *Candida*). Of particular interest to the present invention are species within the genera *Pichia, Kluyveromyces, Saccharomyces, Schizosaccharomyces,* and *Candida*. Of particular interest are the *Saccharomyces* species *S. cerevisiae, S. carlsbergensis, S. diastaticus, S. douglasii, S. kluyveri, S. norbensis,* and *S. oviformis*. Species of particular interest in the genus *Kluyveromyces* include *K. lactis*. Since the classification of yeast may change in the future, for the purposes of this invention, yeast shall be defined as described in Skinner et al., eds. (1980) *Biology and Activities of Yeast* (Soc. App. Bacteriol. Symp. Series No. 9). In addition to the foregoing, those of ordinary skill in the art are presumably familiar with the biology of yeast and the manipulation of yeast genetics. See, for example, Bacila et al., eds. (1978) *Biochemistry and Genetics of Yeast;* Rose and Harrison, eds. (1987) *The Yeasts* ($2^{nd}$ ed.); Strathern et al., eds. (1981) *The Molecular Biology of the Yeast Saccharomyces;* herein incorporated by reference.

The selection of suitable yeast and other microorganism hosts for expression of heterologous proteins is within the skill of the art. When selecting yeast hosts for expression, suitable hosts may include those shown to have, inter alia, good secretion capacity, low proteolytic activity, and overall robustness. Yeast and other microorganisms are generally available from a variety of sources, including the Yeast Genetic Stock Center, Department of Biophysics and Medical Physics, University of California, Berkeley, Calif.; and the American Type Culture Collection, Rockville, Md.

Methods of rPDGF in a yeast host are available in the art. One such method comprises transforming a yeast host cell with a plasmid expression vector comprising a nucleotide sequence encoding human PDGF-BB. This method is briefly described in Example 1 herein and is described in detail in U.S. Pat. No. 6,017,731, and in the copending patent application entitled "Method for Expression of Heterologous Proteins in Yeast," Ser. No. 09/340,250; herein incorporated by reference.

When expressed in a yeast host, rPDGF is secreted as a complex mixture of structural isoforms that result from post-translational processing of the protein during the fermentation production process. Post-translational processing is particularly prevalent in expression of rPDGF-BB. These structural isoforms have varying degrees of biological activity, as demonstrated using standard assays for PDGF activity. Methods of the invention are directed to separation of these structural isoforms such that a final pharmaceutical composition comprising substantially purified isoforms of the greatest biological activity can be prepared. These methods are useful for separating isoforms of rPDGF-AB, and more particularly isoforms of rPDGF-BB.

Recombinant PDGF-BB produced in a yeast host cell is secreted as a fully folded, biologically active homodimeric protein consisting of two highly twisted antiparallel pairs of B chains (Oefner et al. (1992) *EMBO J.* 11:3921–3926). Each B chain comprises 109 amino acid residues. During fermentation to produce a bulk drug substance, several post-translational modifications occur to the secreted rPDGF-BB. This results in a bulk drug substance comprising rPDGF protein having considerable structural heterogeneity. Such modifications include, but are not limited to endoproteolytic digestion between residues Arg-32 and Thr-33 (referred to as "clipping") and exoproteolytic removal of C-terminal amino acids (referred to as "truncation") at Arg-32 and Thr-109, glycosylation of Ser and/or Thr residues, and oxidation of methionine. These post-translational modifications lead to a number of structural forms, or so-called isoforms, of rPDGF-BB present in the secreted product. The structural heterogeneity of the rPDGF-BB yeast product is further complicated by the presence of a rigid Pro-Pro bond at residues 41 and 42. The rotation of this rigid bond is further hindered by its proximity to a disulfide bond and the bulky side chain of Trp-40. This rotational hindrance leads to the formation of stable cis-trans isomers of rPDGF-BB at room temperature. Although numerous potential isoforms exist when considering the multiple combinations of post-translational modifications and Pro-Pro isomerization, isoforms resulting from post-translational clipping and truncation are of primary interest to the present invention.

Figure 2:
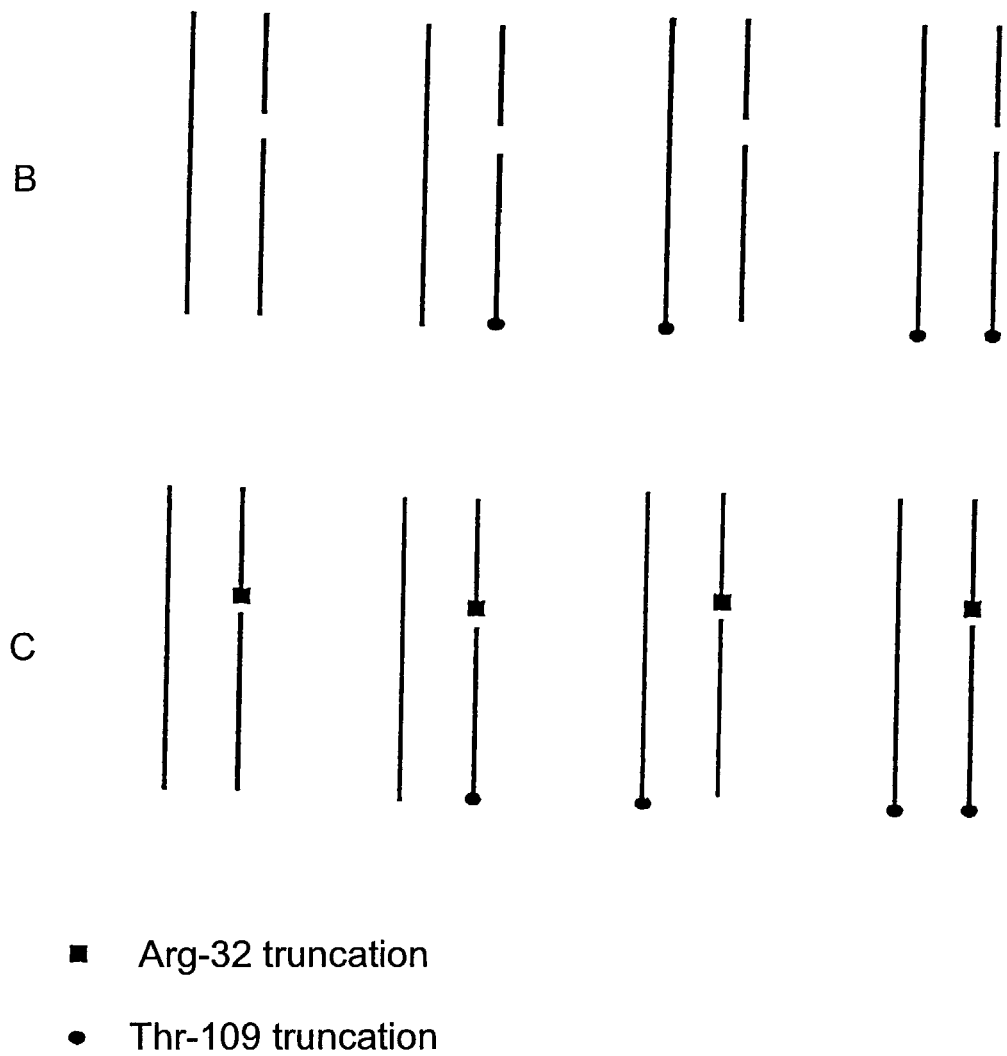
FIG. 2 is a schematic representation of single-clipped isoforms of rhPDGF-BB with or without truncation of Arg-32 and Thr-109. Paired lines represent single-clipped rhPDGF-BB. The clip in one of the B chains is represented by a break in the line. Isoforms of single-clipped species are separated into groups B and C based on the difference in the overall charge of the protein. Truncation of Arg-32 at the clip site (group C) produces a more acidic isoform, while truncation only of Thr-109 (group B) does not alter the molecular charge.
Figure 3:
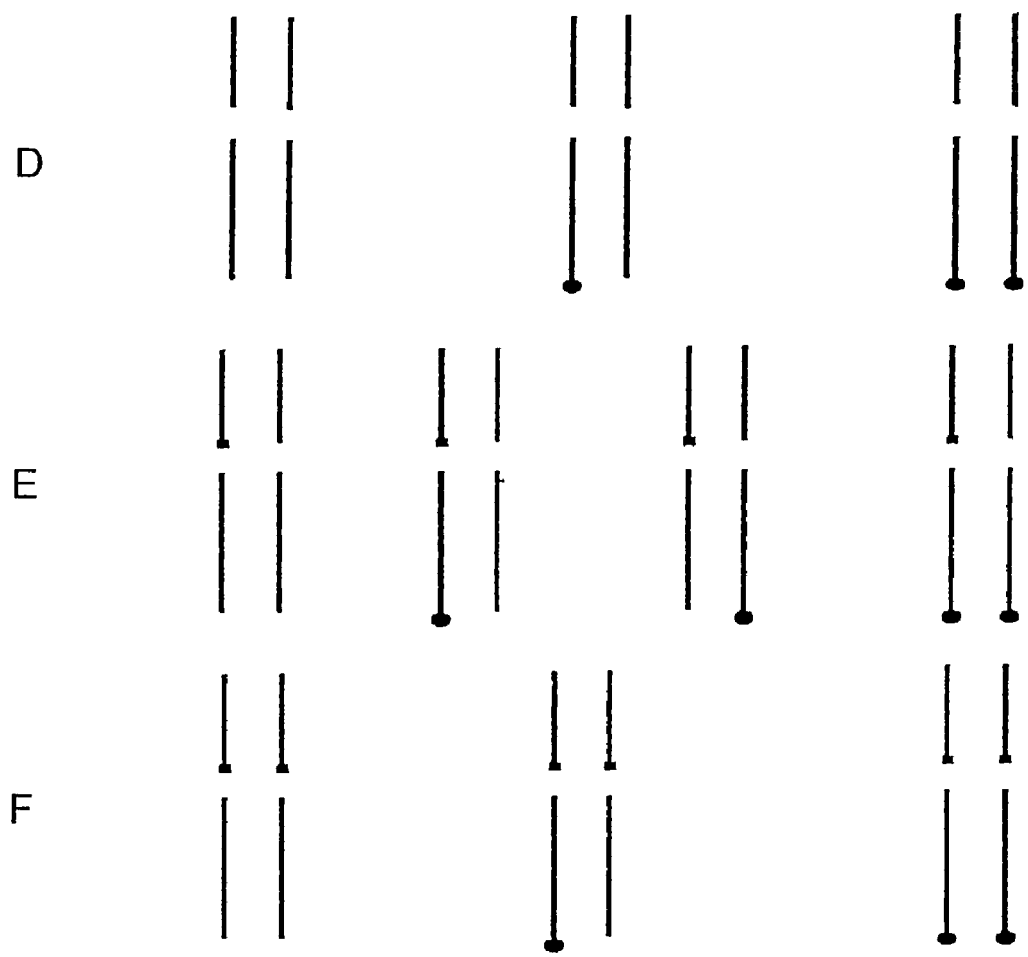
FIG. 3 is a schematic representation of double-clipped isoforms of rhPDGF-BB with or without truncation of Arg-32 and Thr-109. Paired broken lines represent double-clipped rhPDGF-BB. The clip in each of the B chains is represented by a break in each line. The double-clipped isoform is separated into groups D, E, and F based on the difference in the overall charge of the protein. Truncation of the Arg-32 at one of the clip sites (group E) makes the isoform more acidic, while truncation of Arg-32 at both of the clip sites (group F) removes two basic amino acid residues. Truncation only of Thr-109 (group D) does not alter the molecular charge, similar to single-clipped species (group B).
Figure 4:
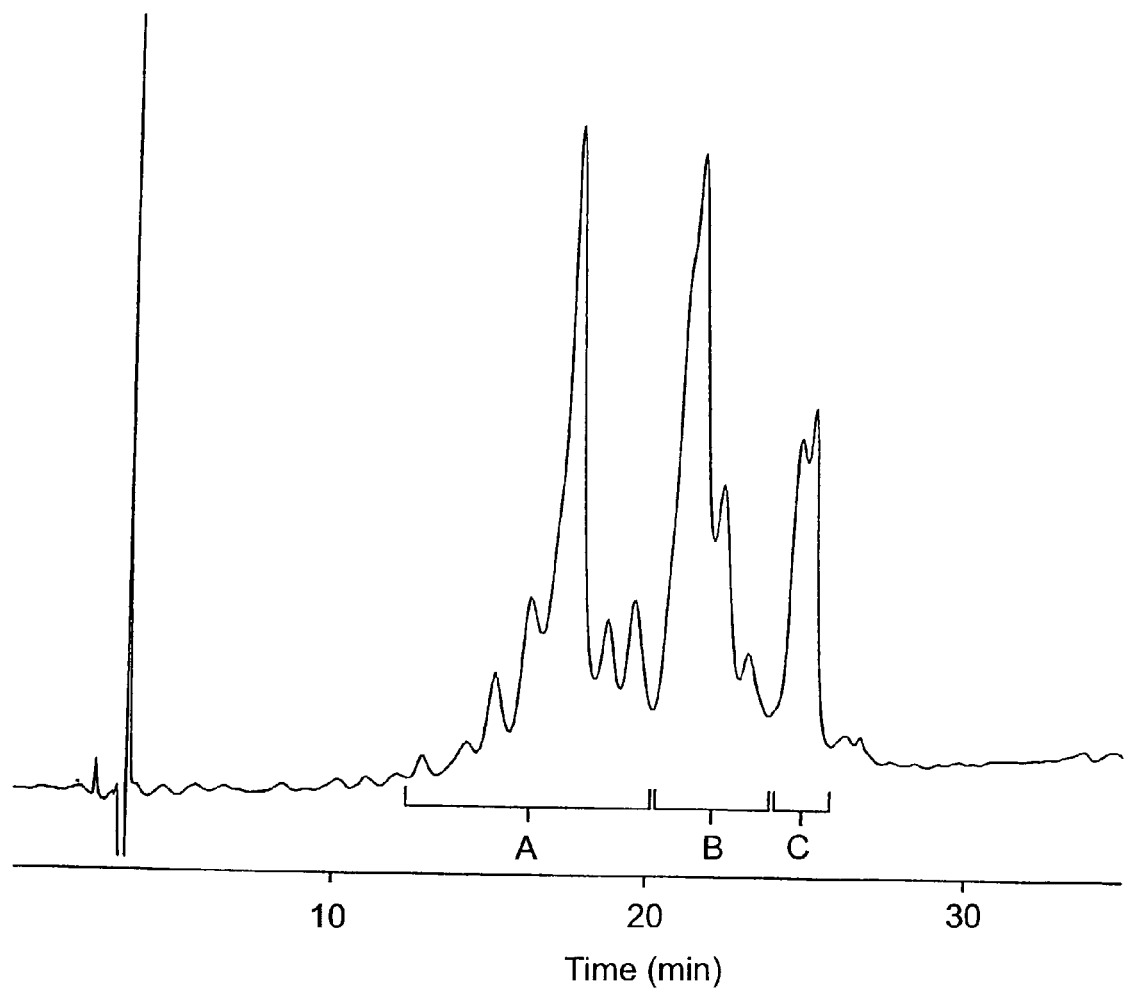
FIG. 4 is a high temperature reverse phase (RP) HPLC profile of rhPDGF-BB using a linear gradient elution. Double-clipped and truncated double-clipped isoforms (A), single-clipped and truncated single-clipped isoforms (B), and intact and truncated intact isoforms (C) of rhPDGF-BB are resolved as three groups of several peaks.
Figure 5:
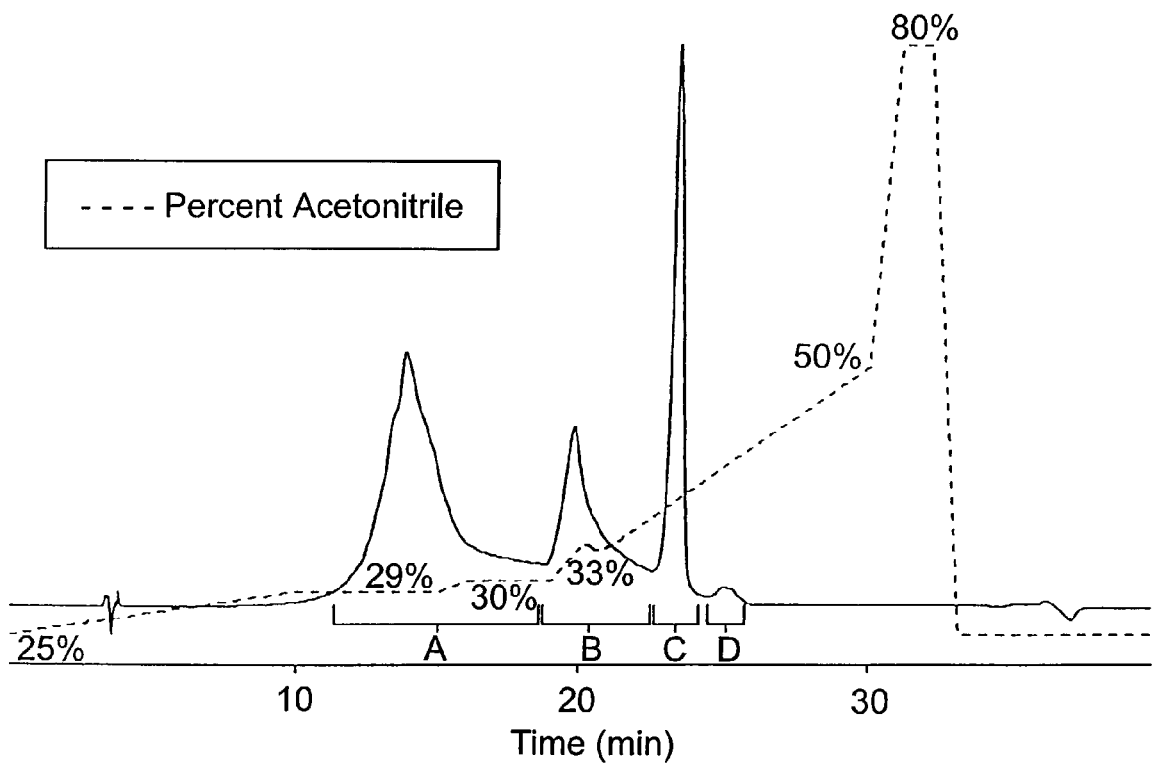
FIG. 5 is a high temperature RP HPLC profile of rhPDGF-BB using a step gradient elution. Double-clipped and truncated double-clipped isoforms (A), single-clipped and truncated single-clipped isoforms (B), intact and truncated intact isoforms (C), and a dimer/dimer (D) of rhPDGF-BB are resolved as individual peaks.
Figure 6A:
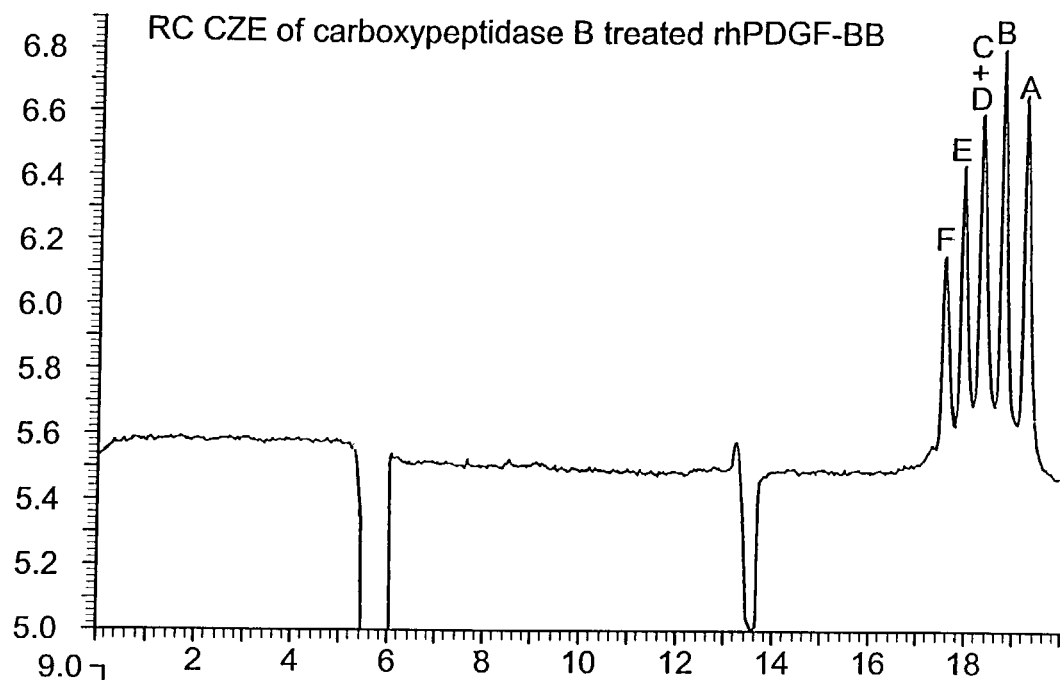
FIG. 6 is an electropherogram of reverse charge capillary zone electrophoresis (RC CZE) of carboxypeptidase B treated PDGF-BB (6B) in comparison to non-treated rhPDGF-BB (6A). Letters correspond to the groups identified in FIGS. 1–3.
Figure 6B:
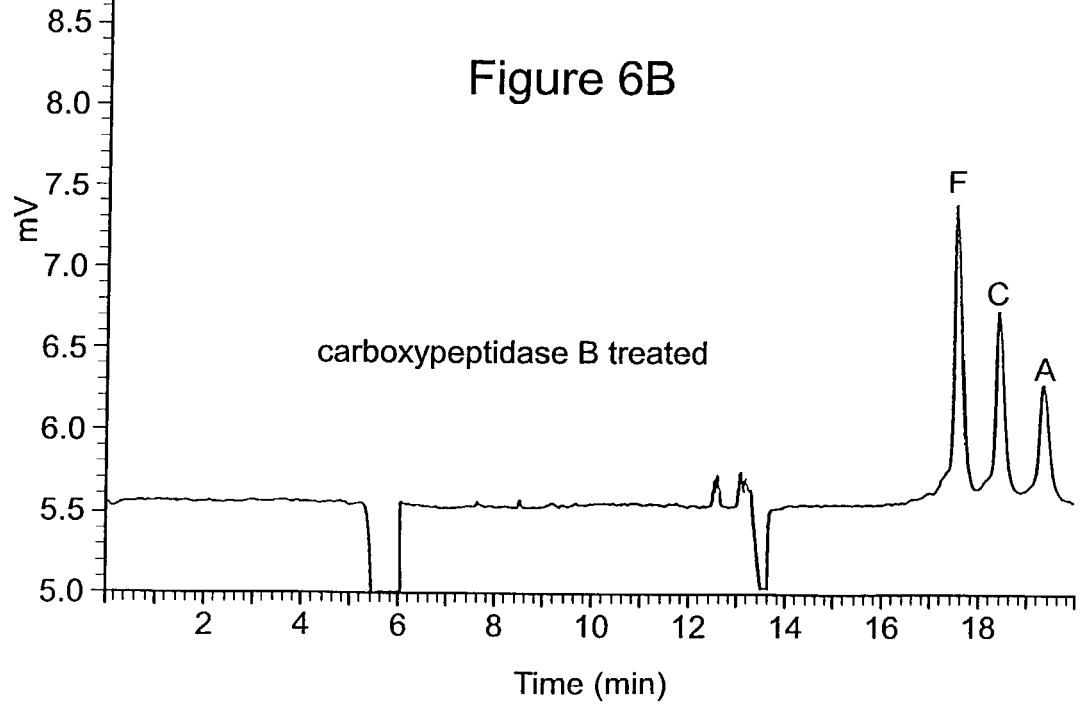

Post-translational endoproteolytic processing or clipping between Arg-32 and Thr-33 leads to three different and distinct basic isoforms of rPDGF-BB: intact, single-clipped, and double-clipped. By "intact" is intended both B chains remain intact and are not endoproteolytically cleaved. By "single-clipped" is intended one B chain is intact and one B chain is endoproteolytically cleaved between Arg-32 and Thr-33. By "double-clipped" is intended both B chains are endoproteolytically cleaved between Arg-32 and Thr-33. Each respective isoform may be additionally modified by C-terminal truncation of Arg-32 or Thr-109, producing a known number of derived structural species for any given basic isoform. Thus, for the intact isoform, C-terminal truncation may occur only at residue 109, leading to three different structural species of that isoform. For the single-clipped isoform, C-terminal truncation of both residues 32 and 109 can produce eight different structural species of that isoform. For the double-clipped isoform, ten structural species of that isoform are possible. All together, the post-translational processes of clipping followed by C-terminal truncation of Arg-32 or Thr-109 residues leads to a complex mixture of twenty-one possible structural isoforms of rPDGF-BB in the bulk drug substance, as illustrated schematically in FIGS. 1–3.

Methods of the invention are directed to separation of the basic isoforms designated as intact, single-clipped, and double-clipped isomers of rPDGF-BB, each of which comprises a known number of derived structural species resulting from truncation of the Arg-32 or Thr-109 residues. It has been determined that the intact isoform has 100% mitogenic activity, the single-clipped isoform has 120% mitogenic activity, and the double-clipped isoform has 20% mitogenic activity. The reference sample exhibits 50% activity. Accordingly, utilizing the methods of the invention compositions can be obtained having at least about 20% greater, preferably at least about 50% greater, more preferably at least about 100% greater PDGF activity than the unpurified cell culture. Thus, for purposes of preparing pharmaceutical rPDGF-BB compositions having use as a therapeutic agent for treatment of wounds, it is clearly desirable to separate these isoforms such that the pharmaceutical compositions comprise intact and/or single-clipped isoforms of rPDGF-BB. Methods of the invention enable preparation of such pharmaceutical compositions by providing for separation of the intact and single-clipped isoforms from the double-clipped isoform of rPDGF-BB of the bulk drug substance produced by fermentation.

Methods of the invention utilize ion exchange enrichment, reverse phase high pressure liquid chromatography, and reverse charge capillary zone electrophoresis. The first of these methods is directed at separation of intact, single-clipped, and double-clipped isomers of rPDGF, particularly rPDGF-BB, where separation is to a degree of purification appropriate for therapeutic use of the rPDGF. Hence, this method is appropriate for separation of these isomers for use in production of a pharmaceutical composition comprising substantially purified intact, single-clipped, or intact and single-clipped rPDGF, particularly rPDGF-BB. The second and third methods, while providing a means for separation of the intact, single-clipped, and double-clipped isomers, are primarily useful for analytical means, as described below.

The intact and single-clipped isoforms of rPDGF-BB can be separated by ion-exchange enrichment from the double-clipped isoform to a degree of purification appropriate for therapeutic use of rPDGF-BB. A bulk drug comprising biologically active rPDGF-BB can be enriched in substantially purified intact and single-clipped rPDGF-BB isoforms by separating these isoforms from the double-clipped isoform using cation exchange chromatography and a TSK sulfopropyl column (TSK SP). The bulk drug substance produced by fermentation, which comprises all three of the isoforms, is run on the column, and the desired isoforms are eluted with NaCl solution. The double-clipped isoform elutes in the earlier fractions, followed by the single-clipped and intact isoforms. Removal of the eluted fraction comprising the double-clipped isoform allows for subsequent collection of fractions eluting the single-clipped and intact isoforms. These fractions can be used separately, or together, to produce a composition comprising the isolated intact isoform, single-clipped isoform, or a mixture of the intact and single-clipped isoforms of rPDGF-BB.

Reverse phase high pressure liquid chromatography (RP HPLC) is a method useful for separating certain isoforms of a dimeric protein preparation having multiple isoforms, where at least one isoform has two different faces. By "face" is intended a term used in the context of RP HPLC, where each polypeptide chain of a dimeric protein is a "face" of the molecule. For homodimers, like PDGF-BB, where the two chains are identical and have no modifications that make one face different than the other, the molecule has but one face. However, where the molecule has, as in the case of rPDGF-BB, a chain that is endoproteolytically cleaved on one of the chains, thus making a single-clipped isoform, the dimer resulting has two faces: the face of the unclipped chain and the face of the clipped chain. A heterodimer naturally has two faces. For example, in the case of the rPDGF-AB heterodimer, the A chain is one face and the B chain is another.

For the purposes of the present invention, RP HPLC conducted at high temperature is used to separate the intact, single-clipped, and double-clipped isoforms of rPDGF-BB. In accordance with the present invention, the RP HPLC method is conducted at a temperature between about 75° C. at a minimum and about 90° C. at a maximum, and more preferably the temperature is about 85° C., for separation of rPDGF-BB isoforms. The RP HPLC method of the invention can further include using a combination isocratic/step gradient of acetonitrile.

Prior to the present application of high temperature RP HPLC to analyze and separate isoforms of rPDGF-BB, it had been noted by researchers producing PDGF-BB in *E. coli* and analyzing it by RP HPLC that at least 4 peaks were routinely observed in the resulting chromatograms (see Watson and Kenney (1992) *J. Chromatography* 606:165–170). It was established that these peaks were due to differences in exposed hydrophobicity caused by a Pro-Pro sequence at residue 41 and 42 (Watson and Kenney (1992) *J. Chromatography* 606: 165–170) and thus measured pro-pro conformers. Furthermore, rPDGF-BB expressed in the yeast *Saccharomyces cerevisae* exhibits multiple conformers that produce broad and heterogenous chromatographic profiles when analyzed with RP HPLC at various ambient and subambient temperatures, as disclosed in Example 3 below. Analysis and separation of rPDGF-BB by RP HPLC at these temperatures is complicated by Pro-Pro isomerizations within the molecule. Additionally, absorptive chromatography cannot simultaneously resolve clipping and truncation to opposing faces of the homodimeric protein under these conditions.

When conducted at high temperature in accordance with the present invention, RP HPLC analysis accelerates the equilibrium of Pro-Pro isomerization as well as accelerating the rate of desorption. As a result, the phenomena of multiple Pro-Pro conformers is not observed. Thus, the number of isoforms potentially resolved can be reduced to the twenty-one structures described earlier as intact, single-clipped, and double-clipped isoforms and their exoproteolyzed species. Furthermore, when RP HPLC analysis is carried out at about 85 C, the heterogeneity resulting from the post-translational modifications due to clipping and truncation occurring on both faces of the dimeric molecule can be resolved.

A combination isocratic/step gradient can also be employed in addition to the high temperature to improve separation of the isoforms, thus greatly simplifying the chromatographic profile. Using the high temperature RP HPLC method with the isocratic/step gradient provides for separation of the isoforms of rPDGF-BB predominantly on the basis of clipping, facilitating analysis and separation of intact, single-clipped, and double-clipped isoforms of rPDGF-BB. Methods for conducting an isocratic/step gradient are available in the art.

Quantities of the intact, single-clipped, and double-clipped isoforms of rPDGF-BB can be separated from a bulk drug substance comprising a mixture of rPDGF isoforms using the RP HPLC method at high temperature and an isocratic/step gradient of acetonitrile in accordance with the present invention. These isoforms can be purified from the acetonitrile and TFA solvent and buffer components. Purification is achieved using standard means for removing proteins from such solvents. For example, dialysis using small tubes, or for larger amounts using continuous flow dialysis fibers, can be conducted to yield a product suitable for use as a therapeutic agent.

The purified rPDGF-BB isoforms obtained in accordance with this method of the invention are useful for conducting biological activity assays to determine relative biological activity of the purified isoforms. In the case of rPDGF-BB, a mitogenic assay to determine the biological activity of a bulk drug substance comprising at least one isoform of rPDGF-BB can be conducted as described in Example 5 disclosed herein.

While the high temperature RP HPLC method of the present invention is useful for separating quantities of isoforms of rPDGF-BB sufficient to analyze biological activity of individual isoforms, the method is not suitable for routine analysis and quantification of the intact and clipped isoforms in a bulk drug substance. The third method of the invention, reverse charge capillary zone electrophoresis (RC CZE) was developed to provide for such quantification and routine analysis.

The reverse charge CZE of the present invention was originally developed to monitor charge heterogeneity since the extremely high isoelectric point (pI=10.5) of the rPDGF-BB molecule precluded the use of conventional isoelectric focusing (IEF) analysis. However, the use of hand cast very high pI IEF gels may be possible.

Separation by RC CZE is based on charge/size ratio. Thus, with respect to the rPDGF-BB of the present invention, truncation of the basic residue Arg-32 has a greater effect on RC CZE assay selectivity than truncation of the neutral amino acid residue Thr-109. Since truncation of the Thr-109 residue does not appreciably alter the charge or size of the protein, there is no separation between the three possible categories of isoforms within the intact isoform. The baseline separation observed between the intact isoform and the single-clipped isoform may be due to an increase in hydrodynamic size of the single-clipped isoform, which may occur through partial denaturation of the secondary structure. Within the single-clipped isoform, the separation of the two species (one without the C-terminal truncation of Arg-32 and the other with that truncation) is due to the decrease in charge of the species of isoform resulting from C-terminal truncation of Arg-32. Within the double-clipped isoforms, three isoforms can be distinguished; the separation of them may be due to the charge difference resulting from either a single or a double C-terminal truncation of Arg-32.

The RC CZE method described thus far is unable to distinguish between, and thus separate, single-clipped isoforms that have the Arg-32 truncation and double-clipped isoforms that do not have the Arg-32 truncation. In order to separate these two isoform categories, and in order to quantify the intact, single-clipped, and double-clipped isoforms, the RC CZE method of the present invention further comprises treating the bulk drug substance comprising the various rPDGF-BB isoforms with carboxypeptidase B prior to analysis. This enzyme is specific for the basic amino acids arginine and lysine located at the carboxy terminus. Enzyme treatment converts single-clipped isoforms not having an Arg-32 truncation to single-clipped isoforms having the Arg-32 truncation, and converts double-clipped isoforms having no, or only one, Arg-32 truncation to isoforms having two Arg-32 truncations. Thus, the treatment of PDGF-BB bulk drug substance with carboxypeptidase B simplifies the RC CZE electropherogram and allows quantification of the three isoforms of rPDGF-BB as defined by the clipping between Arg-32 and Thr-33 (the isoforms referred to as intact, single-clipped, and double-clipped).

The RC CZE method of analysis of PDGF-BB, as modified in the present invention to isolate intact, single-clipped, and double-clipped by use of carboxypeptidase B, is useful, in a quality control context, for analysis of a bulk drug substance comprising the rPDGF-BB isoforms described herein. The advantage of use of RC CZE for analyzing PDGF-BB in a quality control context is the ease and precision achieved by this method, which makes the method an appropriate method for such routine activities of analysis as required in quality control of bulk drug substances.

Thus the methods of the invention are useful in analyzing and separating intact, single-clipped, and double-clipped isoforms of rPDGF-BB. Following separation of the desired intact, single-clipped, or mixture of intact and single-clipped isoforms of rPDGF-BB, contaminating buffer or other impurities can be removed where necessary to produce compositions comprising substantially purified isoforms of interest. These compositions can be prepared for use as a therapeutic agent as described below. By "therapeutic agent" is intended an agent that accomplishes a therapeutic goal, as for example, healing a wound.

Compositions comprising the substantially purified intact, single-clipped, or a mixture of intact and single-clipped isoforms of rPDGF-BB are useful as therapeutic agents in the treatment of wounds, particularly those wounds that are normally repaired in response to the release of the native PDGF.

The release of PDGF in vivo acts as a chemotactic agent to attract monocytes, fibroblasts, and smooth muscle cells to the site of injury, and to initiate cell replication for the purposes of wound repair. This growth factor has been shown to promote healing of incision wounds in rats and healing in regions of the body such as chambers or subcutaneous spaces. Thus PDGF has application in healing such wounds as ulcers, burns, and skin grafts. In addition, PDGF can be used to heal wounds resulting from damaged connective tissue, the repair of which requires fibroblast proliferation and collagen deposition. In addition, where wound healing is retarded by any number of factors including, but not limited to advanced age, diabetes, cancer, and treatment with anti-inflammatory drugs or anticoagulants, PDGF can be used to promote normal wound healing in mammals in situations that would otherwise delay wound healing.

The usefulness of platelet-derived growth factor as a therapeutic agent for full and partial thickness burn repair has also been described by Danilenko et al. (1995) *Am. J. Pathol.* 147:1261–1277. In this manner, recombinant PDGF-BB induces marked extracellular matrix and granulation tissue production such that the burn defects are repaired.

In the context of diabetes, a condition with the complication of delayed wound healing, it has been postulated that refractory diabetic wounds are the result of deficiencies in growth factors and/or cytokines that are important for the healing process. Some preliminary studies have shown that application of certain growth factors or cytokines can facilitate wound healing, as described in Doxey et al. (1995) *Life Sciences* 57(11):111–23. In this study, PDGF of wounded diabetic rats was produced at low levels compared to control animals. These rats had a delayed production of PDGF in cells surrounding the wounds that occurred many days after the wound was incurred, possibly explaining the delay in wound healing in the diabetic animals. Thus, there is a potential application for administration of PDGF-BB to diabetics to induce and normalize wound healing.

Mechanisms of action of PDGF-BB and the other PDGF dimers, including PDGF-AA and PDGF-AB, are discussed generally in Lepisto et al. (1995) *Biochem. Biophys. Res. Comm.* 209(2):393–9. The dimers PDGF-AA and PDGF-BB down-regulate both the steady-state levels of pro-alpha 1 (I), and pro alpha 1 (III) collagen chain mRNAs and the production of collagen, both in a dose-dependent manner.

Additionally, compositions comprising PDGF can facilitate the healing of injured or depleted bones by promoting growth of the connective tissue, growth of the bone and cementum, and by stimulation of protein and collagen synthesis in the region of the injured bone, especially as in the case, for example, of periodontal disease (see WO 88/03409).

Compositions comprising PDGF can provide fast, effective healing for such wounds as, for example, bedsores, lacerations, and burns, as described in WO 91/15231 and U.S. Pat. No. 5,019,559, wherein PDGF in a composition with insulin-like growth factor (IGF) promotes an increase in new connective tissue and an increase in the growth of epithelial tissue.

Compositions comprising PDGF can be administered in a gel formulation, and such a formulation is suitable for topical administration to promote wound healing in conditions such as ulcers, superficial wounds and lacerations, abrasions, surgical wounds, burns, and bone defects, as described in WO 93/08825.

For use as a therapeutic agent for the treatment of wounds, compositions comprising the intact, single-clipped, or a mixture of intact and single-clipped isoforms of PDGF-BB described herein can be administered topically with an appropriate pharmaceutically acceptable carrier or in a substantially purified preparation of protein such that it is free from impurities and elements that would interfere with a therapeutic use. Such preparations that are free of toxic, antigenic, inflammatory, or other deleterious substances and that are at least about 80% pure are considered appropriate. The concentration of the protein can be from about 1 to about 25 µg/ml of total volume, or can be in a range as broad as about 1 ng/ml to about 50 µg/ml depending on the therapeutic use for the rPDGF-BB. A therapeutically effective amount sufficient to accelerate the rate of appearance and increase the number of new fibroblasts in the wound space and to stimulate DNA synthesis in and collagen deposition by those fibroblasts will be in the range of about 1 to about 5 milliliters of the preparation, depending on the characteristics of the wound.

A pharmaceutical composition comprising substantially purified intact or single-clipped isoforms of rPDGF-BB or a mixture of such isoforms and an appropriate pharmaceutically acceptable carrier can be formulated for administration as a therapeutic agent for the treatment of wounds. Pharmaceutically acceptable carriers may be large, slowly metabolized macromolecules such as proteins, polysaccharides, polylactic acids, polyglycolic acids, polymeric amino acids, amino acid copolymers, and inactive viruses in particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. Pharmaceutically acceptable carriers in therapeutic compositions may contain liquids such as water, saline, glycerol, and ethanol. Additionally, auxiliary substances, such as wetting or emulsifying agents, pH buffering substances, and the like, may be present in such vehicles.

The method for formulating a pharmaceutical composition is generally known in the art. A thorough discussion of formulation and selection of pharmaceutically acceptable carriers, stabilizers, and isomolytes can be found in *Remington's Pharmaceutical Sciences*, 18$^{th}$ edition (Mack Pub. Co., Eaton, Pa., 1990).

Typically, the therapeutic pharmaceutical compositions are prepared as injectables, either as liquid solutions or suspensions. Solid forms suitable for solution in, or suspension in, liquid vehicles prior to injection may also be prepared. Liposomes are included within the definition of a pharmaceutically acceptable carrier. Some liposome compositions are described in U.S. Pat. No. 5,422,120; WO 95/13796; WO 94/23697; WO 91/14445; and EP 524,968 B1.

Administration of the PDGF-BB therapeutic pharmaceutical composition can be by any means and to any location of the body of the animal being treated as is appropriate for the wound being treated. Thus, the PDGF-BB can be administered, for example, parenterally or topically. Parenteral administration can include subcutaneous, intravenous, intra-arterial, intramuscular, or direct injection into a region or organ of the body.

The following examples are offered by way of illustration and not by way of limitation.

EXAMPLES

Example 1

Preparation of PDGF-BB Bulk Drug Substance

Recombinant human PDGF-BB (rhPDGF) was produced by a strain of the yeast *Saccharomyces cerevisiae* genetically modified with a multicopy yeast expression plasmid that includes a gene encoding the mature human PDGF-B polypeptide chain. Details of this yeast expression system are disclosed in U.S. Pat. No. 6,017,731, and in the copending application entitled "Method for Expression of Heterologous Proteins in Yeast," Ser. No. 09/340,250; herein incorporated by reference.

The *S. cerevisiae* strain MB2-1 was developed to contain the genotype: Matα, ura3), leu2-3, leu2-112, his3-11, his3-15, pep4), [cir°]. It is auxotrophic for uracil, leucine and histidine, requiring these nutritional supplements when grown in minimal medium. MB2-1 does not contain an endogenous 2-μ plasmid, which tends to interfere with the stability of the introduced plasmids and encourages recombination between endogenous and introduced plasmids. The strain does not express functional protease A, the product of the PEP4 gene, which interferes with the production of heterologous proteins. MB2-1 was designed to impart these favorable characteristics, which include selection for high expression of heterologous proteins.

The vector selected for expressing rhPDGF-BB, pAB24, is a yeast-bacteria shuttle vector. The plasmid is a chimera of sequences from pBR322, derived from several naturally occurring bacterial plasmids, and sequences of the endogenous *S. cerevisiae* 2-μ plasmid (Broach (1981) in *Molecular Biology of the Yeast Saccharomyces* (Cold Spring Harbor Press, New York), 1:445–470). Characteristics of this vector are described in detail in U.S. Pat. No. 6,017,731, and in the copending patent application entitled "Method for Expression of Heterologous Proteins in Yeast," Ser. No. 09/340, 250; herein incorporated by reference.

An expression cassette comprising a nucleotide sequence encoding rhPDGF-BB was ligated into the pAB24 vector to generate the yeast expression plasmid pYL7PPB. Methods for constructing this plasmid and a detailed description of its characteristics are described in detail in U.S. Pat. No. 6,017,731, and in the copending patent application entitled "Method for Expression of Heterologous Proteins in Yeast," Ser. No. 09/340,250; herein incorporated by reference.

Briefly, plasmid pYL7PPB includes an expression cassette with the following features. Transcription initiation and termination are mediated by the inducible hybrid yeast promoter ADH/GAP and the Matα transcriptional terminator. The cassette further includes an open reading frame encoding a truncated yeast alpha-factor leader to mediate secretion of native human proPDGF-B. The prosequence included in the expression construct is only the native N-terminal propeptide encoding sequence; the native C-terminal propeptide sequence was not included in the construct. Inclusion of the N-terminal propeptide resulted in enhanced expression of rhPDGF-BB, as disclosed in copending application Ser. No. 08/989,251. Dibasic processing sites at the truncated alpha factor leader/N-terminal propeptide and N-terminal propeptide/PDGF-B junctions were included to facilitate production of correctly processed rhPDGF-B polypeptide by yeast. The nucleotide and predicted amino acid sequence of open reading frame from pYL7PPB encoding truncated alpha factor leader—proPDGF-B are disclosed in U.S. Pat. No. 6,017,731, and in copending application Ser. No. 09/40,250.

Isolation of the cDNA encoding hPDGF-B was performed using a cDNA library prepared from RNA isolated from a human clonal glioma cell line. The isolation and characteristics of this cDNA have been described in Westermark et al. (1982) *J. Neurosci. Res.* 8:491 and Ponten and Westermark (1978) *Med. Biol.* 56: 184 (1978). This cell line was utilized as a source of RNA for PDGF gene isolation because it had been shown to produce higher levels of PDGF receptor competing activity than other cell lines tested.

Example 2

Enrichment from rhPDGF-BB Bulk Drug Substance of Intact and Single Clipped rhPDGF-BB Isoforms Using TSK Sulfopropyl Cation Exchange Chromatography Making of the rhPDGF-BB bulk drug substance is described in Example 1. The overall goal of this procedure was to generate milligram quantities of intact, single-clipped, and double-clipped isoforms of rhPDGF-BB using repetitive TSK SP 5PW (Tosoh-Haas) chromatography of pure rhPDGF-BB produced in a yeast host cell, then to determine the relative biological activity of the three isoforms using the mitogen assay. In the process, it was shown that when, instead of the 0 to 1 M NaCl called for in the manufacturing protocol, SP TSK 5PW was eluted with a 0

M to 0.6 M NaCl gradient, a significant portion of the double-clipped isoform of rhPDGF-BB appeared to elute at the front of the gradient, separated away from the rest of the material. As the double-clipped isoform is the least biologically active (see examples below), it could be useful to incorporate this simple change (to the 0–0.6 M gradient) in a future, large-scale second-generation process.

The column was prepared by packing 50 ml of TSK SP 5PW (supplied pre-swollen) into an empty Pharmacia column K26 (2.5×10 cm). The packed column was washed with not less than 5 column volumes (c.v.) of loading buffer (0.05 M Na Acetate, pH 4.5). rhPDGF-BB produced by the method of Example 1 was applied, and the column washed with not less than 2 c.v. loading buffer, and then 2 c.v. 0.05 M Na Phosphate pH 7 (with NaOH). The product was eluted with a 10 c.v. linear gradient (from 0 to 0.6 M) NaCl (buffer B) in 50 mM sodium phosphate pH 7.0. The elution peak was fractionated.

In the runs shown here, starting material was a final pool of rhPDGF-BB as described in Example 1. The material was in Na Phosphate at pH 6 at 9.9 mg/ml; the pH was adjusted to 4.5 with 1 M $NaH_3PO_4$. The concentration of rh-PDGF-BB was 9 mg/ml after pH adjustment, and conductivity of the load was 1.62 mS/cm at 25° C. All work was done at room temperature. 477 mg (53 ml) was loaded over the column at 2 ml/min. The column was washed with 2 c.v. of loading buffer (100 ml), and then the 0–0.6 M NaCl gradient was applied in approximately 10 c.v. (492 ml). 15 ml fractions were collected, and fractions were analyzed by PAGE (10–20% Novex Tricine Gels), and absorbencies measure. The protein eluted beginning at fraction 28 through about fraction 50. Based on the gels, fractions 28–30 were pooled, diluted 1:1 with distilled water (to get the conductivity down low enough to permit binding), reapplied to the SP column, and eluted under the same conditions. When analyzed by mitogenic assay, the load was shown to have 14% of the activity of the reference standard, indicating that these fractions represented a large amount of the double-clipped isoform. However, by SDS PAGE gels sufficient analysis could not be made as to quantity of PDGF-BB dimeric isoform. Analysis of these fractions by the RC CZE method described in Example 4 indicates the extent of the purity of the fractions and aids in making an assessment of which fractions contain which isoform and in which relative amounts. By $A_{280}$ the pooled tubes (28–30) were shown to be about 69 mg, or 15% of the 477 mg loaded on for the run. The results of the mitogenic assay conducted with this material indicates low activity and a double-clipped isoform. Analysis of these fractions using RC CZE would then be appropriate for a final determination of the several isoforms isolated, and a quantification of the amounts.

Example 3

High Temperature Linear Gradient RP HPLC Analysis of Nonreduced rhPDGF-BB

The bulk drug substance rhPDGF-BB produced in yeast as described in Example 1 was analyzed on a 5 micron, 300 Angstrom, Delta-Pak C3 (3.9 mmID×15 cm L) column using a Spectra Physics 8800 solvent delivery pump equipped with a WISP 712 autoinjecter and a PE 135 diode array detector. Column temperature was controlled by the use of a Nesslab glycol cooling bath of a Jones Chromatography heating block. The separation was achieved at a 1.2 ml/min flow rate using a 5 to 60% acetonitrile/0.1% TFA linear gradient over 40 minutes.

When rhPDGF-BB was analyzed at 5° C., six distinct peaks with several smaller shoulders were resolved. As the temperature increased (5° C., 20° C., 33° C., 60° C.), the profile became less defined. However, at 60° C. the peak became more resolved although shoulders were still present. The early-eluting doublet peak (24 minutes) observed in the 5° C. profile disappeared as the temperature was increased. To further characterize the distinct peaks generated at 5° C., the rhPDGF-BB was semi-preparatively fractionated. These fractions were analyzed by RP HPLC and each fraction rechromatographed, resulting in a profile that displayed significant amounts of protein present in other fractions. Thus, it is apparent that a slow but reversible equilibrium exists between isoforms separated at 5° C. resulting from the interconversion of rhPDGF-BB conformers. Isomerization of the Pro-Pro bond is probably responsible for the observed slow equilibrium among rhPDGF-BB conformers.

The RP HPLC analysis of nonreduced rhPDGF-BB was then performed using a Zorbax 300SB-C18 reversed-phase column (4.6 mm ID×25 cm L) maintained at 85° C. using a linear TFA/acetonitrile gradient. This method resolved the 21 predicted clipped and truncated isoforms of rhPDGF-BB, which are clustered into three major groups (intact, single-clipped, and double-clipped). Fractions collected across each group were analyzed using RP HPLC of reduced rhPDGF-BB. The results indicated that the multiple peaks in each group are due to different levels of C-terminal truncation of Arg-32 and Thr-109. Further attempts to improve the separation of clipped and intact isoform from these three groups were unsuccessful using a linear gradient. Thus, high temperature at a linear gradient of RP HPLC was able to resolve the heterogeneity resulting from post-translational modifications due to clipping and truncation occurring on both faces of the molecule, and the phenomena of multiple Pro-Pro conformers was not observed at high temperature.

A combination isocratic/step gradient was then employed in addition to the high temperature to improve separation of the isoforms. The high temperature step gradient resolved the double-clipped isoform at 29% acetonitrile, the single-clipped isoform at 30% acetonitrile, and the intact isoform at 33% acetonitrile. Unlike the linear gradient above, isoforms due to truncation are not resolved, and thus simplify the profile greatly. Accordingly, separation of the isoforms of rhPDGF-BB predominantly on the basis of clipping was achieved by the high temperature combination isocratic/step gradient just described, therefore simplifying the chromatographic profile greatly, and facilitating analysis and separation of key functional isoforms of rhPDGF-BB.

Example 4

Reverse Charge Capillary Zone Electrophoresis Assay for rhPDGF-BB Including Pretreatment with Carboxypeptidase B A sample of rhPDGF-BB recombinantly produced in yeast as described in Example 1 and a reference material having a known composition of PDGF-BB were assayed using reverse charge capillary zone electrophoresis (RC CZE). The samples of interest were diluted in running buffer having Tris buffer at pH 8.0 to a concentration of 1.0 mg/ml as determined by spectrophotometry. 100 μl of 25 U/ml carboxypeptidase B was added to 50 μl of test sample. After 30 minutes of incubation at room temperature, 25 μl of 0.1N HCl was added. A sequence table was prepared on a Turbochrom Sequence Screen. Degas reagents necessary for carrying out the assay were prepared by placing 1500 μl of each of the following into a separate 1700 μl polypropylene microfuge tube: 1N NaOH, cCAP™ Regenerator solution, and 50 mM Tris buffer (pH 8.0). The tubes were microfuged for 5 minutes at the highest rpm setting available.

The assay was run on a capillary electrophoresis system (BioFocus™ 3000) configured with the following information: prep 1: preinject NaOH, 180 sec; prep 2: preinject AMREGEN, 180 sec; prep 3: preinject AMRINSE 180 sec; pressure: 2 psi*sec; polarity: neg to pos; voltage: 15.00 kV; current limit: 50.00 uA; inlet buffer: AMRUN; outlet buffer: AMRUN; cartridge temp: 25 degrees Celsius; run time: 10 min; single wavelength programmable detector mode; and lamda(nm): 214. The samples were loaded into the BioFocus™ 3000. Enable Peak detection was set prior to rise in the electropherogram before the double-clipped peak and Disable Peak detection was set after the horizontal line following the intact rhPDGF-BB peak. The electopherogram was acceptable if the difference in duplicate sample measurements was less than 10%.

The results of analysis of clinical lots of rhPDGF-BB by RC CZE indicated the following compositions of intact, single-clipped, and double-clipped isoforms for material intended for commercial use:

| batch | double-clipped | single-clipped | intact |
|-------|----------------|----------------|--------|
| 1 | 47% | 31% | 22% |
| 2 | 44% | 33% | 23% |
| 3 | 45% | 33% | 22% |
| 4 | 46% | 33% | 21% |
| 5 | 45% | 33% | 22% |
| 6 | 45% | 32% | 23% |

Example 5

Mitogenic activity of Single-clipped, Double-clipped and Intact Isoforms of rhPDGF-BB The ability of PDGF to stimulate DNA synthesis and cell growth in culture can be tested by $^3$H-Thymidine incorporation into DNA of cultured cells responsive to PDGF, and results in the demonstration of biological activity of PDGF or PDGF-like molecules. Such an assay is described in U.S. Pat. No. 4,849,407, and in Cook et al. (1992) *Biochem. J.* 281:57–65, herein incorporated by reference. This is a standard assay for determining potential therapeutic benefit of PDGF.

The mitogenic assay for PDGF, a mitogen, is believed in the art to represent potential usefulness as a pharmaceutical composition. It has been determined previously that the C-terminal truncations do not have any effect on the biological activity. It has also determined that over the narrow range of peak elution, the acetonitrile and triflouroacetic acid (ACN-TFA) components of the chromatography had a consistent effect on the mitogenic assay.

Purified single-clipped, double-clipped and intact forms of rhPDGF-BB were collected through repeated cycles of high temperature nonreduced RP HPLC. The single-clipped, double-clipped and intact forms were tested using the high temperature nonreduced and reduced RP HPLC assays, and the purities were found to be 95%, 97%, and 95%, respectively. Samples of each form were then tested by the mitogenic activity assay. All samples were assayed in triplicate in the same assay. The fractions of each isoform were collected, and it was determined that the single-clipped isoform had 120% activity, the intact isoform had 100% activity, and the double clipped had 20% activity. The reference sample (an unpurified cell culture comprising a mixture of intact, single-clipped, and double-clipped isoforms of rhPDGF-BB) exhibited 50% activity. This indicated that it may be desirable to remove the double-clipped isoform in a rhPDGF-BB bulk substance that is intended for therapeutic use.

Example 6

PDGF-BB to Treat a Wound

A PDGF-BB mixture of intact and single-clipped isoforms is prepared in a topical cream. Application of about 50 to about 100 mM of PDGF-BB mixture is made to a third degree burn wound from 1 to 3 times daily for a month, or until the wound is healed. Standard application procedures for dressing burn wounds are practiced for the administration of the PDGF-BB cream to the burn wound.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for preparing a composition enriched in intact and single-clipped isoforms of biologically active recombinant PDGF (rPDGF)-BB dimeric protein from a mixture of isoforms of said rPDGF-BB dimeric protein, wherein the rPDGF-B polypeptides in said rPDGF-BB dimeric protein are native-sequence or variant rPDGF-B polypeptides that exhibit at least about 80% sequence identity to native-sequence rPDGF-B polypeptides, said method comprising taking said mixture and enriching said mixture in said intact and single-clipped isoforms by reducing amounts of undesired isoforms in said mixture to obtain said composition.

2. The method of claim 1, wherein said enriching is accomplished using ion exchange chromatography, reverse phase high-pressure liquid chromatography, or reverse charge capillary zone electrophoresis.

3. The method of claim 2, wherein the rPDGF-B polypeptides are native-sequence polypeptides.

4. The method of claim 3, wherein the rPDGF-B polypeptides have the amino acid sequences of human rPDGF-B polypeptides.

5. The method of claim 2, wherein said rPDGF-BB is produced in a yeast host cell.

6. The method of claim 5, wherein said yeast host cell is a *Saccharomyces* yeast host cell.

* * * * *